United States Patent
Johannesson et al.

(10) Patent No.: US 7,502,102 B2
(45) Date of Patent: Mar. 10, 2009

(54) SYSTEM AND METHOD OF IMAGING THE CHARACTERISTICS OF AN OBJECT

(75) Inventors: Mattias Johannesson, Linkoping (SE); Mats Gokstorp, Vreta Kloster (SE)

(73) Assignee: Sick IVP AB, Linkoping (SE)

( * ) Notice: Subject to any disclaimer, the term of this patent is extended or adjusted under 35 U.S.C. 154(b) by 0 days.

(21) Appl. No.: 10/574,390

(22) PCT Filed: Sep. 24, 2004

(86) PCT No.: PCT/SE2004/001375

§ 371 (c)(1),
(2), (4) Date: Dec. 19, 2006

(87) PCT Pub. No.: WO2005/031326

PCT Pub. Date: Apr. 7, 2005

(65) Prior Publication Data

US 2007/0096044 A1    May 3, 2007

(30) Foreign Application Priority Data

Oct. 1, 2003    (SE) .................................. 0302603

(51) Int. Cl.
*G01N 21/86* (2006.01)
*G01V 8/00* (2006.01)

(52) U.S. Cl. .............. 356/237.2; 356/237.1; 356/239.1; 250/559.41; 250/559.4

(58) Field of Classification Search ... 356/237.1–237.6, 356/601–636; 250/559.41, 559.4, 559.45, 250/208.1

See application file for complete search history.

(56) References Cited

U.S. PATENT DOCUMENTS

| | | | |
|---|---|---|---|
| 4,188,544 A | | 2/1980 | Chasson |
| 4,460,273 A | * | 7/1984 | Koizumi et al. .......... 356/237.2 |
| 4,725,139 A | | 2/1988 | Hack et al. |

(Continued)

FOREIGN PATENT DOCUMENTS

JP    2001305072 A    10/2001

(Continued)

OTHER PUBLICATIONS

Seltman, Joachim; "Indication of slope-of-grain and biodegradation in wood with electromagnetic waves"; *Seminar/Workshop on Scanning Technology and Image Processing on Wood*; Sep. 1, 1992, pp. 1-16; The Royal Institute of Technology; Stockholm Sweden.

*Primary Examiner*—Sang Nguyen
(74) *Attorney, Agent, or Firm*—Townsend and Townsend and Crew LLP

(57) ABSTRACT

A system and method for imaging the characteristics of an object (2) having at least a first (2a) and a second (2b) layer. The object (2) is illuminated by means of incident light (4), and light (5b) reflected from the object (2) is detected by means of an imaging sensor (6) in which the detected light is converted into electrical charges, according to which a representation of the object (2) is created. Information on light scattered (5a) in the first layer (2a) and the second layer (2b) of the object (2) is obtained from the representation and this information is compared to stored information in order to detect defects on the object (2).

16 Claims, 7 Drawing Sheets

U.S. PATENT DOCUMENTS

| | | | |
|---|---|---|---|
| 4,886,975 A * | 12/1989 | Murakami et al. | 250/559.41 |
| 5,278,012 A * | 1/1994 | Yamanaka et al. | 430/30 |
| 5,293,538 A * | 3/1994 | Iwata et al. | 356/239.1 |
| 5,334,844 A | 8/1994 | Pollard et al. | |
| 5,416,594 A | 5/1995 | Gross et al. | |
| 5,936,726 A * | 8/1999 | Takeda et al. | 356/237.2 |
| 6,256,093 B1 * | 7/2001 | Ravid et al. | 356/237.2 |
| 6,590,656 B2 * | 7/2003 | Xu et al. | 356/369 |
| 6,734,960 B1 * | 5/2004 | Goto et al. | 356/237.1 |
| 6,831,742 B1 * | 12/2004 | Sui et al. | 356/369 |
| 6,956,658 B2 * | 10/2005 | Meeks et al. | 356/600 |

FOREIGN PATENT DOCUMENTS

| | | |
|---|---|---|
| JP | 2003247952 A | 9/2003 |
| WO | WO 02/12869 A1 | 2/2002 |

\* cited by examiner

SYSTEM AND METHOD OF IMAGING THE CHARACTERISTICS OF AN OBJECT

BACKGROUND OF THE INVENTION

1. Field of the Invention

The present patent application relates to the field of imaging the characteristics of an object, and particularly to a measuring system allowing for detecting defects of an object by imaging the characteristics of the object having at least a first and a second layer as well as a method for such detection.

2. Description of the Related Art

Quality control is very important in for instance the packaging industry. Most manufacturers perform a manual visual inspection of the products, i.e. examining the products with the human eye. This is time consuming, expensive, not very efficient and may be considered to be a subjective evaluation. An alternative to the manual quality inspection is to use an automated inspection system. However, the inspection of transparent or semi-transparent materials is difficult since defects on these materials are invisible to normal inspection systems.

One method of inspecting transparent objects, such as glass or plastics, is to use a bright-field/dark-field system. The bright-field is the region where specular reflected light from the object is imaged on a sensor. The dark-field is the region in which diffusely reflected light from the object is imaged on a sensor. The signals from the dark- and bright-field sensors can be used to detect defects on the surface of transparent objects. When no defect is present, the bright-field image is bright and the dark-field image is dark. But, when the object has a defect, the dark-field image presents an increased brightness. However, this method of inspecting transparent objects only detects defects on a surface layer.

One prior art approach is disclosed in EP 902 275, which suggests an imaging apparatus and process for inspecting an object wrapped in a transparent or semi-transparent material, such as a cigarette package wrapped in a polymeric film. Incident light is directed upon the object such that the light enters the wrapper and the wrapper acts as a waveguide. The light escapes from the poly film wrap at edges and folds where it reaches a reflective boundary. The escaped light is captured by a camera and is thereafter sent to an imaging processor. Thus, overwrap defects, such as misplacement, misfolding, tearing, wrinkling or other defects, will be detected.

However, this prior art approach only detects defects in a wrapping layer. Defects on the package itself must be separately inspected at a separate stage requiring more than one inspection system, manual or automatic.

Therefore, there is a need for a system and a method for the detection of defects on an object comprising at least two layers, where at least the first layer consists of a transparent or semi-transparent material.

SUMMARY OF THE INVENTION

Accordingly, it is an object of the present invention to provide an improved measuring system allowing for imaging the characteristics of an object having at least a first and a second layer.

This object is achieved through providing a measuring system comprising at least one light source arranged to illuminate the object with incident light, an imaging sensor arranged to detect reflected light from the object and to convert the detected light into electrical charges and, means for creating a representation of the object according to the electrical charges, wherein the device comprises means for obtaining information on light scattered in the first layer and the second layer of the object from the representation and, means for comparing the information to stored information in order to detect defects on the object.

Another object of the invention is to provide an improved method for imaging the characteristics of an object having at least a first and a second layer.

This object is achieved through a method of providing a measuring system, in which the object is illuminated by means of incident light, and light reflected from the object is detected by means of an imaging sensor in which the detected light is converted into electrical charges, according to which a representation of the object is created, whereby information on light scattered in at least a first layer and a second layer of the object is obtained from the representation and that the information is compared to stored information in order to detect defects on the object.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 2b discloses how light scatters when a second layer of an object to be examined has a defect according to the first example corresponding FIG. 2a;

FIG. 3b discloses how light scatters when a second layer of an object to be examined has a defect according to the second example corresponding FIG. 3a;

FIG. 4b discloses how light scatters when a first layer of an object to be examined has a defect according to the third example corresponding FIG. 4a;

FIG. 5b discloses a captured image on a two-dimensional sensor over an object to be examined shown in FIG. 5a;

FIG. 7b discloses a captured image on a two-dimensional sensor over an object to be examined shown in FIG. 7a;

DETAILED DESCRIPTION OF THE PRESENTLY PREFERRED EMBODIMENTS

Figure 1:
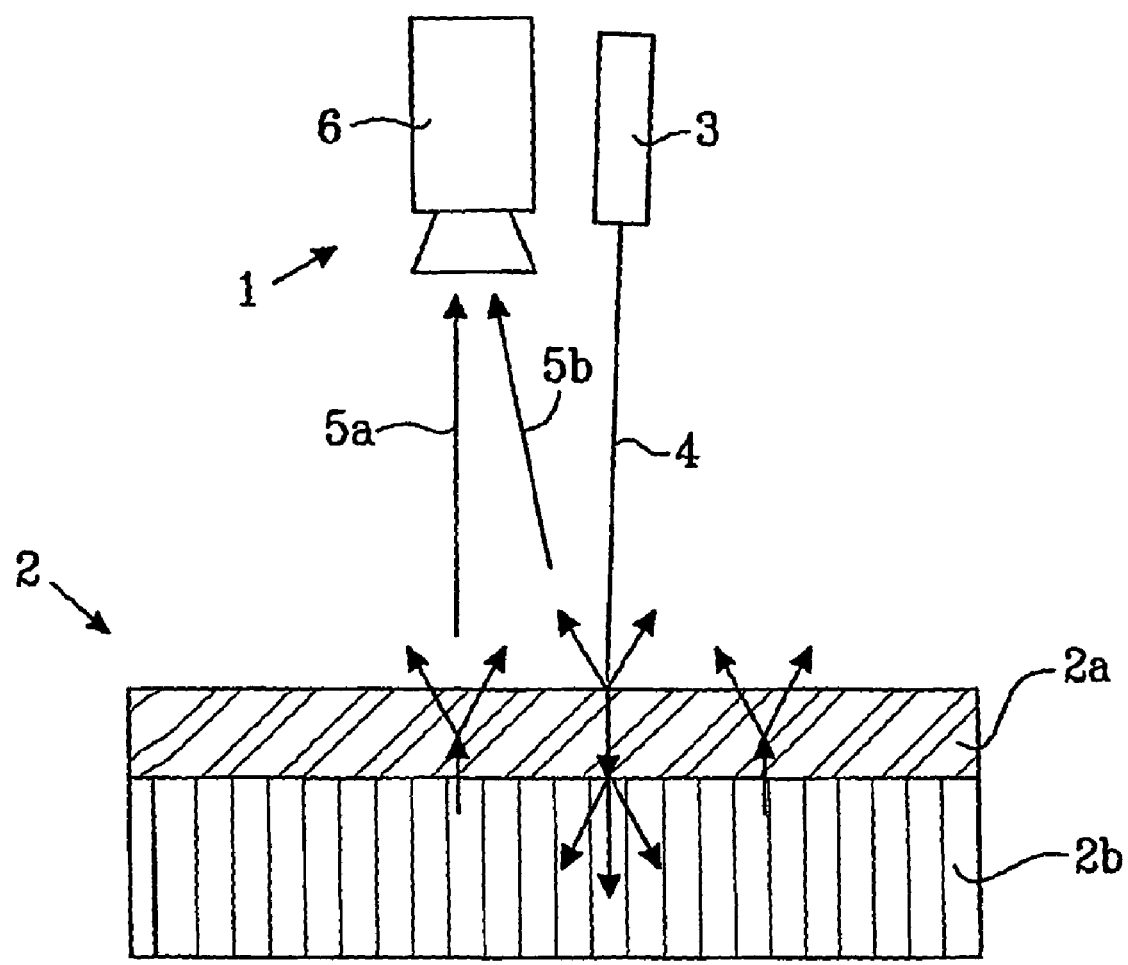
FIG. 1 discloses a schematic view of a measuring system according to a first embodiment of the invention.

FIG. 1 is a conceptual diagram showing a basic constitution of a measuring system 1 for imaging the characteristics of an object 2 having at least a first 2a and a second 2b layer according to a first embodiment of the present invention. The system 1 comprises at least one light source 3 arranged to illuminate the object 2 with incident light 4. An imaging sensor 6 is arranged to detect reflected light 5a and 5b from the object 2 and to convert the detected light into electrical charges. Reflected light which is detected by the imaging sensor 6 is denoted 5b and, light scattered in the object which is detected by the imaging sensor 6 is denoted 5a. The system further comprises means for creating an analogue or digital representation of the object 2 according to the electrical charges, such as an image/signal-processing unit (not shown). Said means for creating the analogue or digital representation of the object 2, may either be a separate unit or integrated in the imaging sensor 6. In the preferred embodiment of the present invention, a digital representation of the object 2 is created.

The object 2 and the measuring system 1 are moved in relation to one another in a predefined direction of movement on parallel planes, preferably in a substantially horizontal direction. In the preferred embodiment of the present invention the object 2 moves relative to the measuring system 1. The object 2 may e.g. be placed on a conveyor belt which moves or alternatively there is no belt and the object itself moves, for example, if said object is paper in a continuous web in a paper-making machine. Instead of the object 2 moving relative to the measuring system 1, the relationship may naturally be reversed, that is to say the object 2 is stationary and the measuring system 1 moves over the object 2 when measuring. In still another embodiment both the object 2 and the measuring system 1 move in relation to each other.

The incident light has limited dispersion in at least one direction. Thus, the light source 3 generate, for example, point light, linear light or light composed of multiple, substantially point or linear segments and may be of any type suitable to the application, for example a laser, a light-emitting diode (LED), ordinary light (light bulb), which are familiar to the person skilled in the art and will not be further described herein.

The light source 3 comprises in one embodiment of the present invention a polarizer (not shown), which polarises the incident light 4. This facilitates in making a distinction between reflected and scattered light, since the reflected light also will be polarized but the scattered light will be polarised to a lesser degree. When the light source 3 comprises a polarizer, it is necessary to use a sensor that distinguish between light polarized in different directions.

The imaging sensor 6 may be a CCD camera, a CMOS camera, or any other sensor suitable for imaging characteristics of an object.

The system further comprises means for obtaining information on light scattered in the first layer 2a and/or the second layer 2b of the object 2 from the digital representation. This read out information is compared with stored information, such as a threshold value, in order to detect defects on or in the object 2, e.g. the light intensity in each point of the digital representation may be compared to a predetermined value. The type of defect can in this manner be classified. Other well-known classification methods are of course possible to use, such as comparing the relative light intensity between two adjacent points of the digital representation with a predetermined value, etc.

The object 2 may for example be a laminated product comprising two or more different materials or, comprising two or more layers of the same material assembled with different directions of the grain of the material. Or, may be a package wrapped in a transparent or semi-transparent material, such as a foil, which may be laminated or unlaminated. More examples are food wrapped in or covered by a transparent or semi-transparent material, such as a plastic, or an electronic component, such as a printed circuit board, covered by a protecting layer. The thickness of the layers may be equal or different. The first layer may be only a layer of lacquer. The invention is not limited to any specific example of objects. The invention is based on that some materials scatter light very well and that the scattered light is affected by the underlying or overlying material (layer).

Some examples of detected and classified defects are listed below and illustrated in FIGS. 2a-4b. All of the illustrated examples comprise two layers, but the invention works well on objects having more than two layers. Information of the object to be inspected is stored, i.e. what the "normal" image on the sensor should look like (how light normally is reflected and scattered). Depending on which divergence from the "normal" image the captured image has, the type of defect can be classified.

Figure 2A:
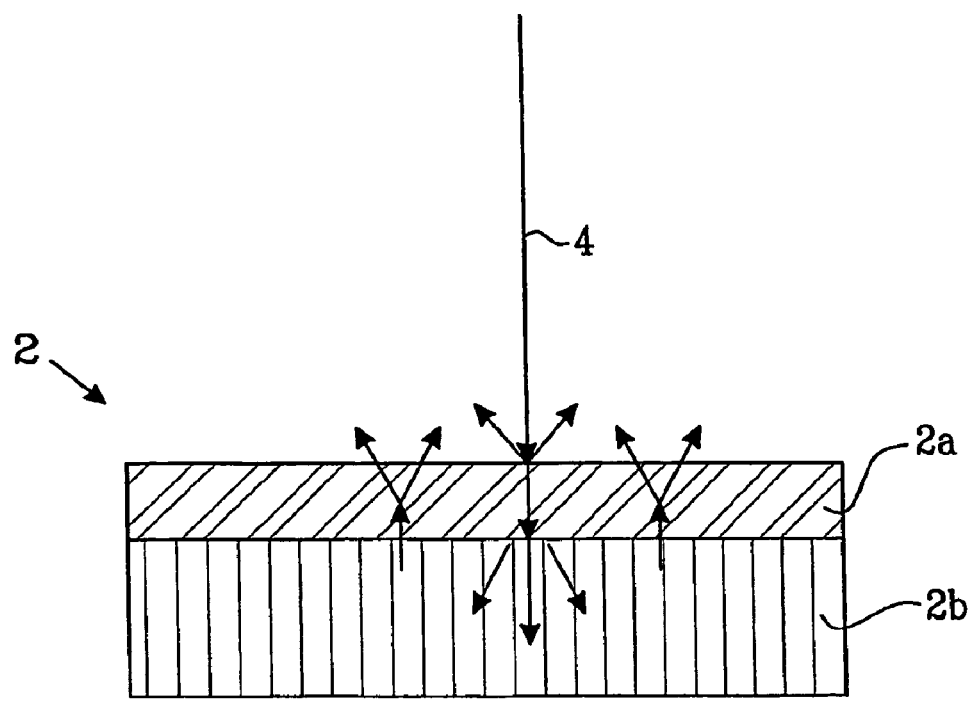
FIG. 2a discloses a view of an object to be examined showing how light normally scatters in the different layers in a first example of how defects are detected and classified with the inventive system.
Figure 2B:
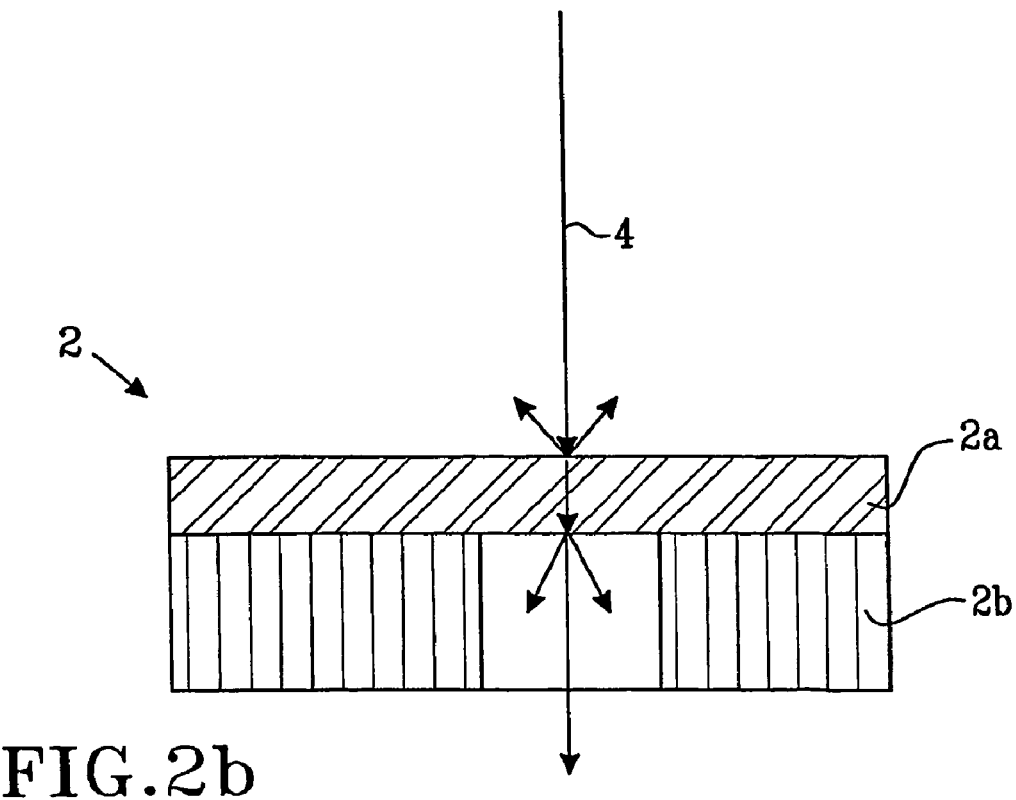

FIGS. 2a and 2b illustrates a first example of a defect detected and classified by the inventive system, where the first layer 2a transmits light and the second layer 2b scatters light. FIG. 2a shows incident light 4 which hits the first layer 2a, some of the incident 4 light is reflected and some of it enters the first layer 2a. The entered light is transmitted through the first layer 2a and enters the second layer 2b where it is scattered. The scattered light re-enters the first layer 2a, is transmitted therethrough and leaves the first layer 2a whereby it is detected by the sensor 6 (shown in FIG. 1).

If, however, the second layer 2b has a defect, there will be a reduction of the scattered light detected by the imaging sensor. In this simplified example, shown in FIG. 2b, the sensor will only detect reflected light.

Figure 3A:
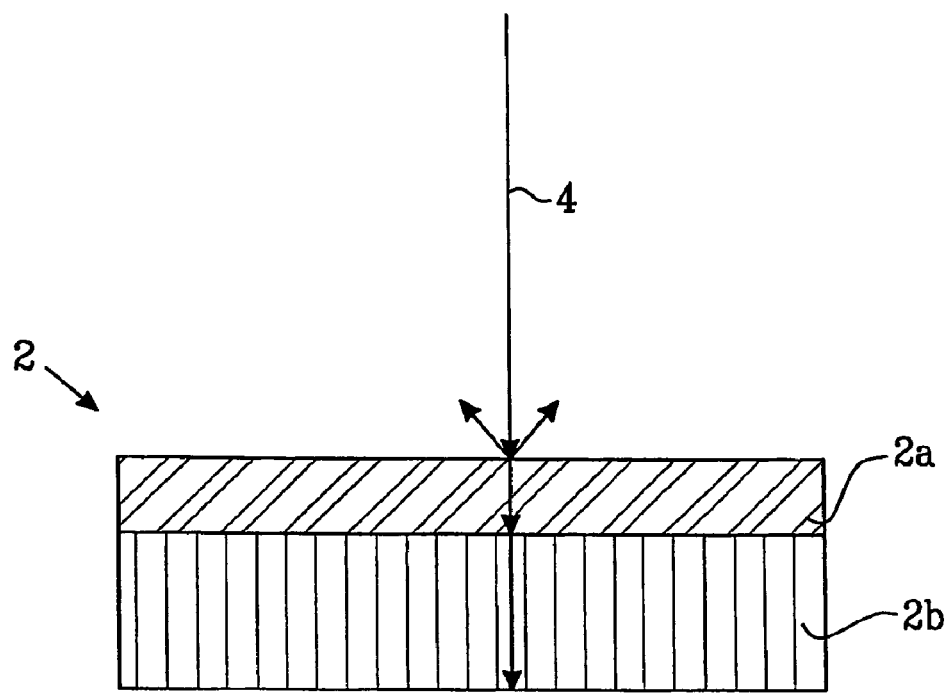
FIG. 3a discloses a view of an object to be examined showing how light normally scatters in the different layers in a second example of how defects are detected and classified with the inventive system.
Figure 3B:
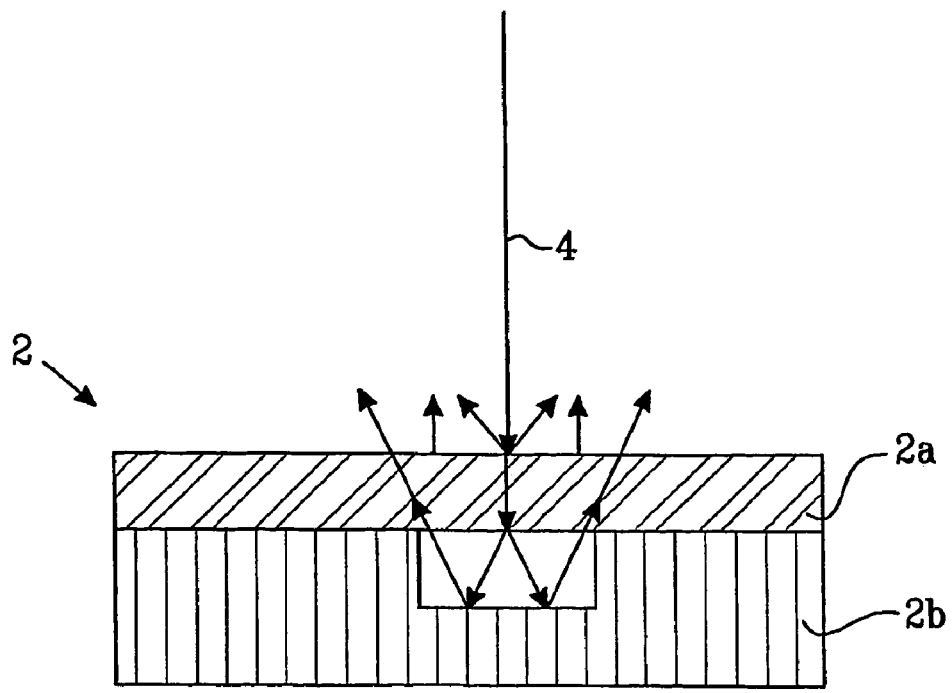

FIGS. 3a and 3b illustrates a second example of a defect detected and classified by the inventive system, where both the first layer 2a and the second layer 2b transmit light. Incident light 4 hits the first layer 2a some of which is reflected and some of which enters the first layer 2a. The entered light is transmitted through the first layer 2a and enters the second layer 2b, through which it is also transmitted.

If, however, the object 2 is delaminated, i.e. there is a space between the first 2a and the second 2b layer, there will be an increase of scattered light detected by the imaging sensor, shown in FIG. 3b. This is due to the reflection of the light on the second layer 2b leading to increased scattered light.

Figure 4A:
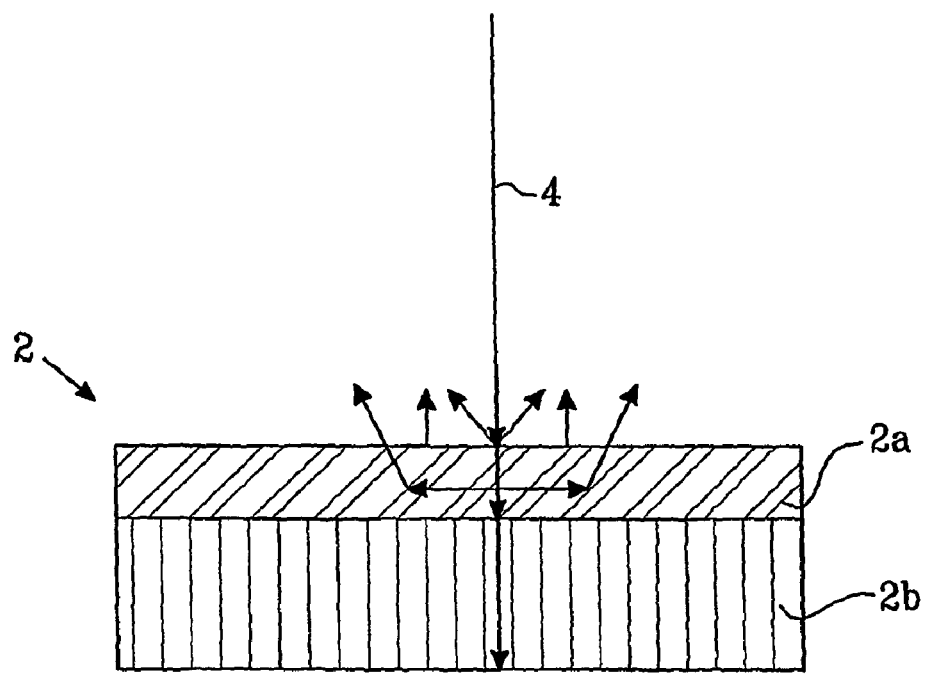
FIG. 4a discloses a view of an object to be examined showing how light normally scatters in the different layers in a third example of how defects are detected and classified with the inventive system.
Figure 4B:
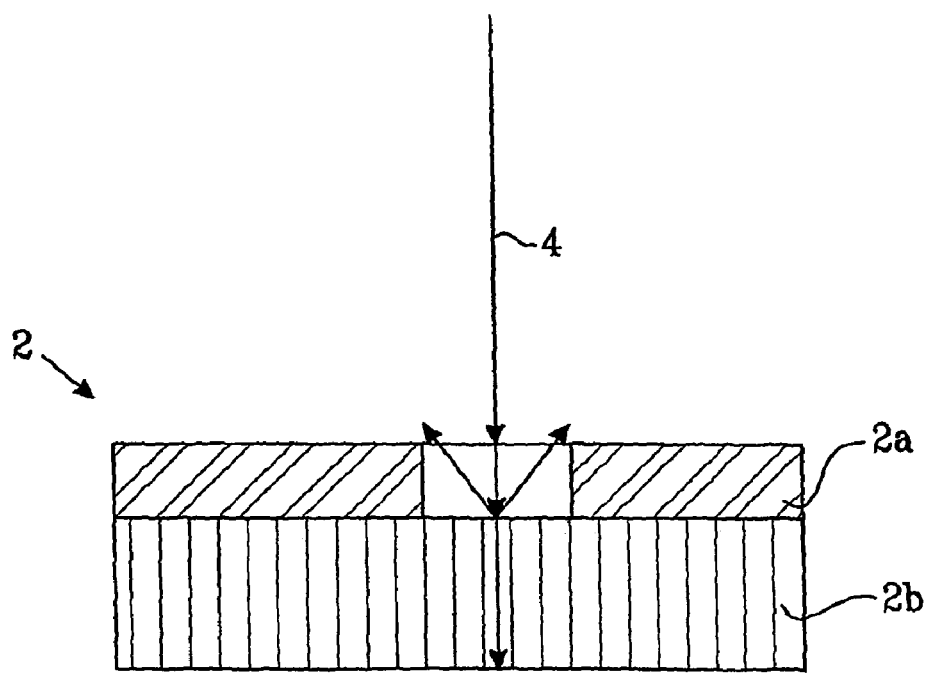

FIGS. 4a and 4b illustrates a third example of a defect detected and classified by the inventive system, where the first layer 2a scatters light and the second layer 2b transmits light. Incident light 4 hits the first layer 2a some of which is reflected and some of which enters the first layer 2a. The entered light is partly transmitted through the first layer 2a and partly scattered therein. The scattered light leaves the first layer 2a and is detected by the imaging sensor. The transmitted light enters the second layer 2b and is transmitted therethrough.

If, however, there is a defect on the first layer 2a such as a missing piece, there will be a reduction of scattered light detected by the imaging sensor. In the example shown in FIG. 4b, only reflected light on the second layer 2b is detected by the imaging sensor.

Another example (not shown) of a defect detected and classified by the inventive system, is where the first layer scatters light and the second layer 2b reflects light. If there is a defect on the second layer, such as a missing piece, a reduction of the scattered light will be detected by the imaging sensor.

Figure 5A:
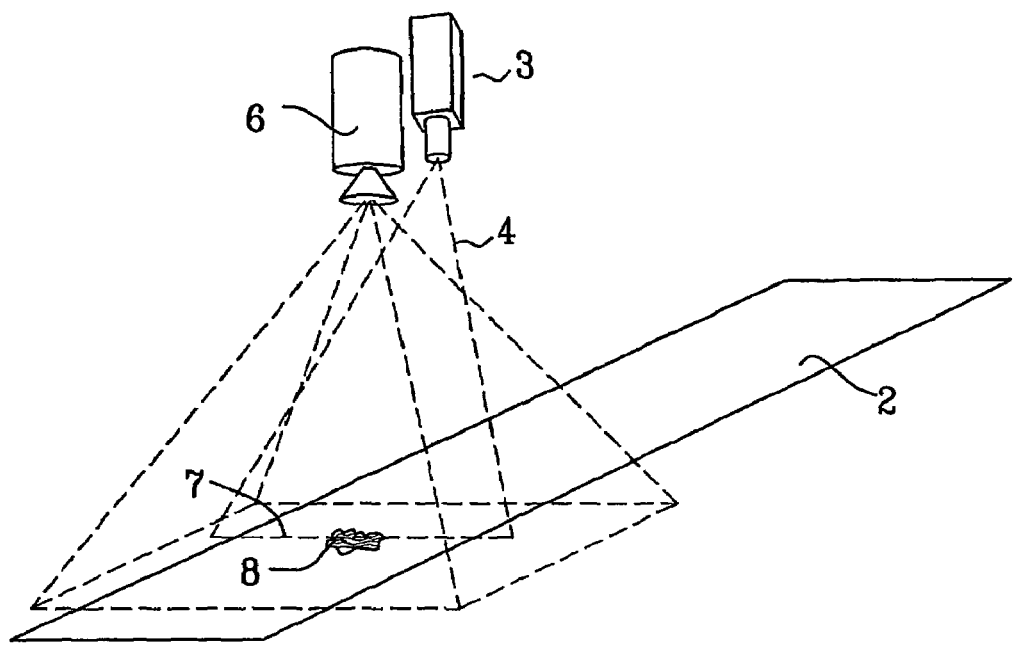
FIG. 5a discloses a schematic view of a measuring system according to the first embodiment of the invention, where an object to be examined comprises a defect.

FIG. 5a illustrates the measuring system according to the first embodiment of the present invention corresponding to FIG. 1. The system 1 comprises at least one light source 3 arranged to illuminate the object 2 with incident light 4. An imaging sensor 6 is arranged to detect reflected light from the object 2. In this embodiment the light source 3 has generated a line of light 7 across the object 2. The object 2 comprises a defect 8 which in FIG. 5a is located within the field of view (FoV) of the imaging sensor 6.

Figure 5B:
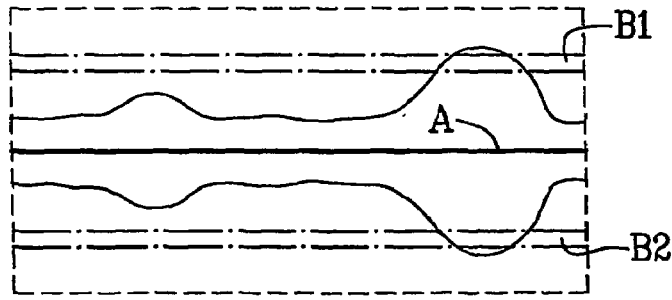

The image of the object in FIG. 5a captured on the two-dimensional sensor 6 is shown in FIG. 5b. The sensor detects both the light scattered in the regions B1 and B2 in the object 2 and the reflected light A on the object 2. FIG. 5b shows the line of light 7 (shown in FIG. 5a) as A. On both sides of the reflected light A an area of scattered light appears which can be seen in FIG. 5b.

If the light source 3 comprises a polarizer, the regions B1 and B2 may be moved closer to the line of light A on the object 2 without cross-talk between the reflected and scattered measurements. This enables detection of small defects.

Figure 5C:
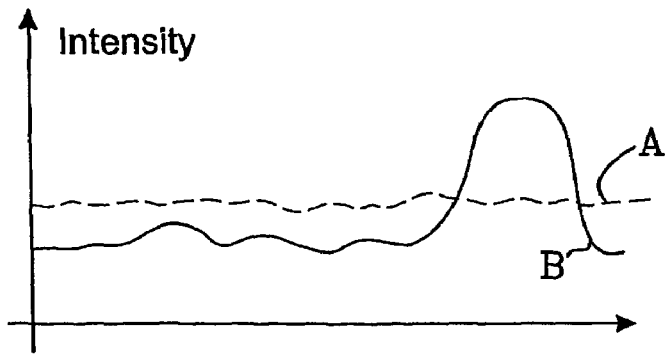
FIG. 5c discloses the measured intensities of the captured image shown in FIG. 5b.

The intensities (signal strengths) of the reflected light A and the scattered light B in the captured image in FIG. 5b are shown in FIG. 5c. The indicated defect 8 which yields an increased scatter is clearly visible in FIG. 5c.

If the complete image is retrieved from the sensor, the processing to find the intensity of the scattered and reflected light is made by an external signal-processing unit. The output of raw sensor information limits, however, the possible sampling speed. If the sensor has random access capability it is possible to extract only the interesting regions from the sensor, thus retrieving a smaller amount of data from the sensor and a possibility to reach a greater sampling speed. With some sensors it is also possible to have different exposure time and/or read-out amplification for the two regions and also to sum the scattered light from a number of rows to further increase the signal strength.

The scattered light may be collected on one side, B1 or B2, of the reflected light or summed up from both sides, B1 and B2, to further increase the signal strength. If a point light source is used, a multitude of positions may be used together or independent of each other to determine the amount of scattered light. Thus, information on the main direction of the scattered light may be obtained.

Figure 6:
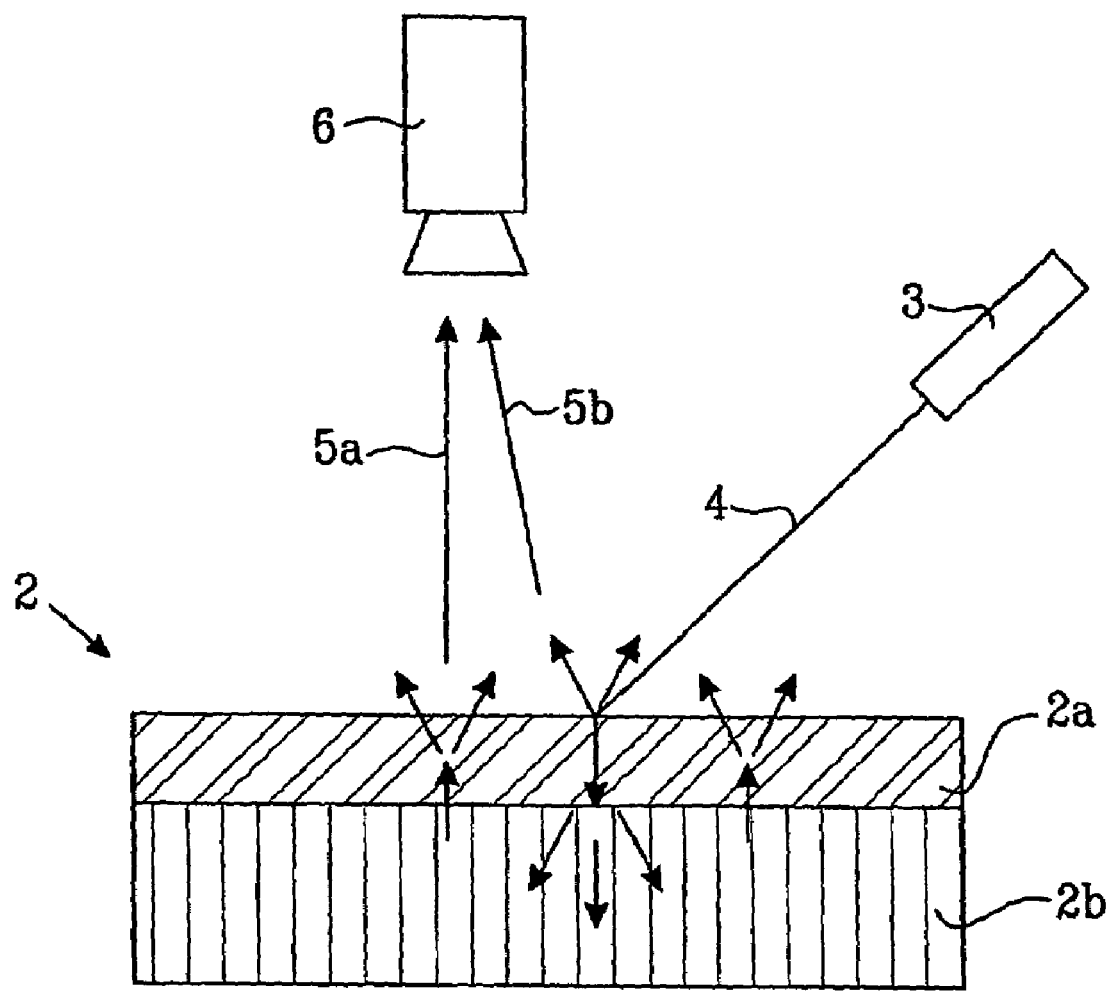
FIG. 6 discloses a schematic view of a measuring system according to a second embodiment of the invention, where a three-dimensional image is obtained.

FIG. 6 shows a setup of the inventive measuring system according to a second embodiment of the present invention. In this embodiment, the system 1 comprises one light source 3 arranged to illuminate the object 2 with incident light 4. An imaging sensor 6 is arranged to detect reflected light 5a and 5b from the object 4 and to convert the detected light into electrical charges. Reflected light which is detected by the imaging sensor 6 is denoted 5b and, light scattered in the object which is detected by the imaging sensor 6 is denoted 5a. The system further comprises means for creating an analogue or digital representation of the object 2 according to the electrical charges, such as an image/signal-processing unit (not shown). In the preferred embodiment a digital representation is created. Said means for creating the digital representation of the object 2, may either be a separate unit or integrated in the imaging sensor 6. In this setup of the measuring system 1, the light source 3 is placed at a distance away from the imaging sensor 6 in order to besides obtaining information on scattered light also obtaining information on the geometric profile of at least one of the layers 2a or 2b of the object 2 from the digital representation.

The information on the geometric profile of the object 2, i.e. the object shape information, is obtained by using triangulation, i.e. the position of the reflected light indicates the distance from the sensor 6 to the object 2.

The setups in FIGS. 1 and 6 comprise a single light source 3. It is, however obvious for the person skilled in the art that more than one light source can be used. For example, in the second embodiment of the present invention shown in FIG. 6, different light sources may be used for the three-dimensional (geometry) and the two-dimensional (scattered light) images. This can even increase the imaging speed in some cases.

Figure 7A:
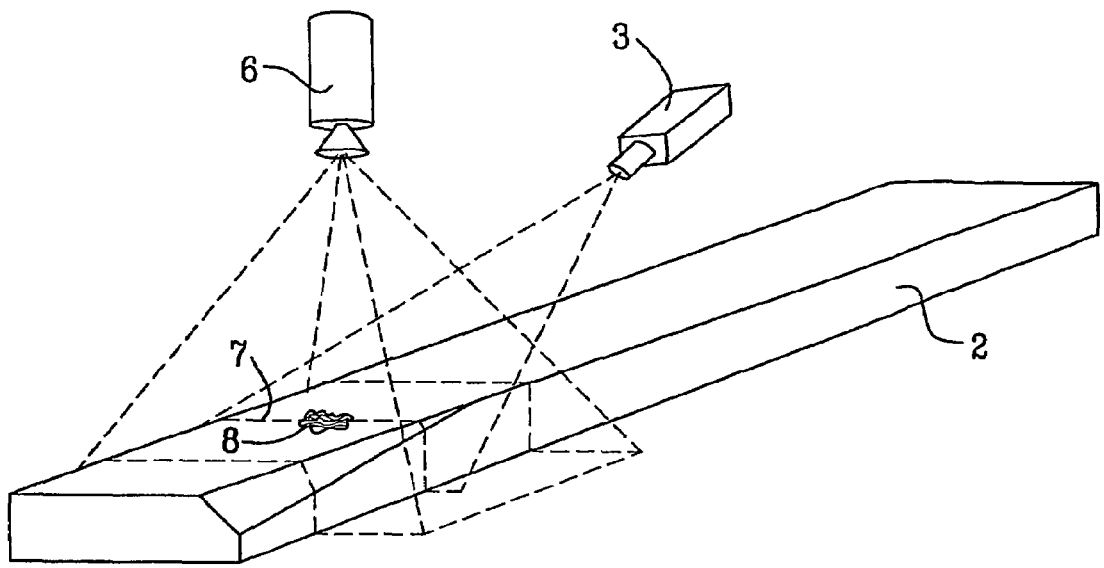
FIG. 7a discloses a schematic view of a measuring system according to the second embodiment of the invention, where an object to be examined comprises a defect.

FIG. 7a illustrates the measuring system according to the second embodiment of the present invention corresponding FIG. 6. The system 1 comprises at least one light source 3 arranged to illuminate the object 2 with incident light 4. An imaging sensor 6 is arranged to detect reflected light 5 from the object 2. In this embodiment the light source 3 has generated a line of light 7 across the object 2. The object 2 comprises a defect 8 which in the FIG. 7a is located within the field of view (FoV) of the imaging sensor 6.

Figure 7B:
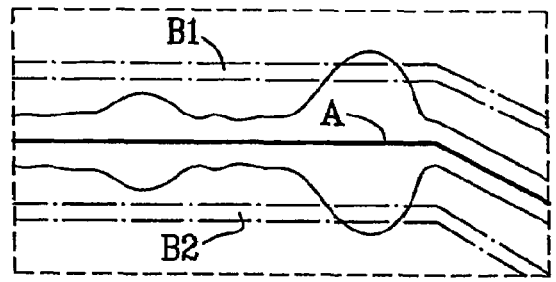

The image of the object in FIG. 7a captured on the two-dimensional sensor 6 is shown in FIG. 7b. FIG. 7b shows the line of light 7 (shown in FIG. 7a) as A. On both sides of the reflected light A an area of scattered light appears which can be seen in FIG. 7b. The sensor detects both the light scattered in the regions B1 and B2 in the object 2 and the reflected light in A on the object 2. The shape (geometry) of the object 2 is shown with the bold line A in FIG. 7b. The geometry of the object (indicated with C in FIG. 7c) follows line A, i.e. the reflected light. The regions B1 and B2 are in parallel with line A.

Figure 7C:
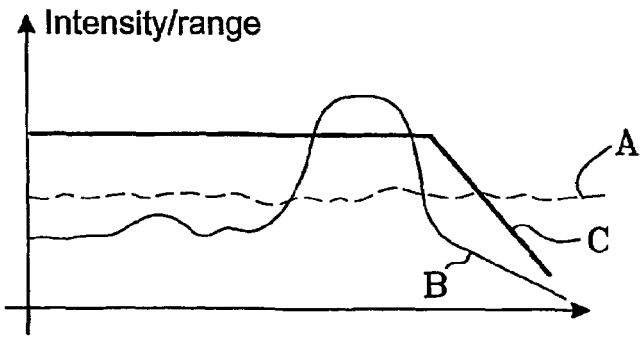
FIG. 7c discloses the measured intensities/range profile of the captured Image shown in FIG. 7b.

The intensities (signal strengths) of the reflected light A and the scattered light B in the captured image in FIG. 7b are shown in FIG. 7c. The indicated defect 8 which yields an increased scatter is clearly visible in FIG. 7c. FIG. 7c further shows the range profile C extracted from the shape of A shown in 7b.

In the following will be described a method for imaging the characteristics of an object having at least a first and a second layer by means of a measuring system, in which method the object is illuminated by means of incident light, and light reflected from the object is detected by means of an imaging sensor in which the detected light is converted into electrical charges, according to which a representation of the object is created, wherein information on light scattered in the first layer and the second layer of the object is obtained from the representation and that the information is compared to stored information in order to detect defects on the object.

In a further embodiment of the method the measuring system and/or the object is/are moved in relation to one another in a predefined direction of movement.

In another embodiment the method further comprises the step of obtaining information on the geometric profile of the object from the representation, either the first layer of the object or the second layer of the object.

In still another embodiment the method further comprising the step of using polarized incident light in order to facilitate the distinction between reflected light on the object and scattered light in the object.

As illustrated by the above, a measuring system and a method for imaging the characteristics of an object having at least a first and a second layer by means of the measuring system has been described, where defects may be detected in both the first and the second layer. The approach according to the present invention being advantageous in comparison to the previously discussed prior art approach, which detects defects in only a wrapping layer of an object The present invention eliminates these restrictions of such a prior art approach through enabling the detection of defects in either one of the first and the second layer of the object or both.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A measuring system for detecting defects of an object having at least a first and a second layer, which system comprises at least one light source arranged to illuminate the object with incident light, a single two-dimensional imaging sensor arranged to detect reflected light emanating from the object and to convert the detected light into electrical charges, and means for creating a representation of the object according to the electrical charges, wherein the system comprises means for obtaining information from the representation of light scattered by entering the object and emerging from the object at a different location from the entering location after being spread in the first layer and the second layer of the object from the representation, and means for comparing the information to stored information in order to detect defects on the object.

2. A measuring system according to claim 1, wherein the measuring system and/or the object is/are arranged to move in relation to one another in a predefined direction of movement.

3. A measuring system according to claim 1, wherein the incident light is arranged to have limited dispersion in a predefined direction.

4. A measuring system according to claim 3, wherein the incident light is a linear light.

5. A measuring system according to claim 1, wherein the system further comprises means for obtaining information on the geometric profile of the object from the representation.

6. A measuring system according to claim 5, wherein the system comprises means for obtaining information on the geometric profile of the first layer of the object from the representation.

7. A measuring system according to claim 5, wherein the system comprises means for obtaining information on the geometric profile of the second layer of the object from the representation.

8. A measuring system according to claim 1, wherein the light source comprises a polarizer arranged to facilitate the distinction between light reflected on the object and scattered light in the object.

9. A measuring system according to claim 1, wherein the first layer consist of a transparent or semi-transparent material.

10. A measuring system according to claim 1, wherein the object is a package wrapped in a protective material.

11. A method for detecting defects of an object having at least a first and a second layer by means of a measuring system, in which method the object is illuminated by means of incident light, and light reflected and emanating from the object is detected by means of a single two-dimensional imaging sensor in which the detected light is converted into electrical charges, according to which a representation of the object is created, wherein information is obtained from the representation of en light scattered by entering the object and emerging from the object at a different location from the entering location after being spread in the first layer and the second layer of the object and wherein the information is compared to stored information in order to detect defects on the object.

12. A method according to claim 11, wherein the measuring system and/or the object is/are moved in relation to one another in a predefined direction of movement.

13. A method according to claim 11, wherein also information on the geometric profile of the object is obtained from the representation.

14. A method according to claim 13, wherein information on the geometric profile of the first layer of the object is obtained from the representation.

15. A method according to claim 13, wherein information on the geometric profile of the second layer of the object is obtained from the representation.

16. A method according to claim 11, wherein the incident light is polarized and wherein the polarized incident light is used to distinguish between reflected light on the object and scattered light in the object.

* * * * *